US009078925B2

(12) United States Patent
DeBoeck et al.

(10) Patent No.: US 9,078,925 B2
(45) Date of Patent: *Jul. 14, 2015

(54) PHARMACEUTICAL SEMI-SOLID COMPOSITION OF ISOTRETINOIN

(71) Applicants: Arthur M. DeBoeck, Gurabo, PR (US); Francis Vanderbist, Brussels (BE); Cecile Servais, Mehaigne (BE); Philippe Baudier, Brussels (BE)

(72) Inventors: Arthur M. DeBoeck, Gurabo, PR (US); Francis Vanderbist, Brussels (BE); Cecile Servais, Mehaigne (BE); Philippe Baudier, Brussels (BE)

(73) Assignee: GALEPHAR PHARMACEUTICAL RESEARCH, INC., Humacao, PR (US)

(*) Notice: Subject to any disclaimer, the term of this patent is extended or adjusted under 35 U.S.C. 154(b) by 0 days.

This patent is subject to a terminal disclaimer.

(21) Appl. No.: 14/133,073

(22) Filed: Dec. 18, 2013

(65) Prior Publication Data

US 2014/0107203 A1    Apr. 17, 2014

Related U.S. Application Data

(63) Continuation-in-part of application No. 13/713,897, filed on Dec. 13, 2012, and a continuation-in-part of application No. 13/525,857, filed on Jun. 18, 2012, and a continuation-in-part of application No. 13/525,904, filed on Jun. 18, 2012.

(51) Int. Cl.
| | |
|---|---|
| A61K 47/44 | (2006.01) |
| A61K 47/14 | (2006.01) |
| A61K 31/203 | (2006.01) |
| A61K 9/00 | (2006.01) |
| A61K 47/10 | (2006.01) |
| A61K 9/48 | (2006.01) |
| A61K 9/107 | (2006.01) |

(52) U.S. Cl.
CPC ............... *A61K 47/44* (2013.01); *A61K 9/0014* (2013.01); *A61K 9/4858* (2013.01); *A61K 9/4866* (2013.01); *A61K 9/4875* (2013.01); *A61K 31/203* (2013.01); *A61K 47/10* (2013.01); *A61K 47/14* (2013.01); *A61K 9/1075* (2013.01)

(58) Field of Classification Search
USPC .................................................. 514/559, 769
See application file for complete search history.

(56) References Cited

U.S. PATENT DOCUMENTS

| | | |
|---|---|---|
| 4,464,394 A | 8/1984 | Bollag |
| 5,185,264 A | 2/1993 | Makela |
| 5,252,604 A | 10/1993 | Nagy et al. |
| 5,993,858 A | 11/1999 | Crison et al. |
| 6,020,003 A | 2/2000 | Stroh et al. |
| 6,054,136 A | 4/2000 | Denis et al. |
| 6,248,363 B1 | 6/2001 | Patel et al. |
| 6,267,985 B1 | 7/2001 | Chen et al. |
| 6,294,192 B1 | 9/2001 | Patel et al. |
| 6,383,471 B1 | 5/2002 | Chen et al. |
| 6,593,292 B1 | 7/2003 | Rothbard et al. |
| 6,624,154 B1 | 9/2003 | Benoit et al. |
| 6,923,988 B2 | 8/2005 | Patel et al. |
| 2002/0025338 A1 | 2/2002 | Pant et al. |
| 2003/0077297 A1 | 4/2003 | Chen et al. |
| 2004/0009225 A1 | 1/2004 | Vanderbist et al. |
| 2007/0026062 A1 | 2/2007 | Holm et al. |
| 2013/0189318 A1* | 7/2013 | Holm ............................ 424/400 |
| 2013/0217769 A1 | 8/2013 | Vanderbist et al. |

FOREIGN PATENT DOCUMENTS

| | | |
|---|---|---|
| CA | 2762391 | 11/2000 |
| CA | 2423170 | 3/2002 |
| CA | 2762391 | 11/2010 |
| EP | 0 184 942 | 6/1985 |
| EP | 0 184 942 | 6/1986 |
| RU | 2400226 | 9/2010 |
| WO | WO 85/03434 | 8/1985 |
| WO | WO 00/00179 | 1/2000 |
| WO | WO 00/25772 | 5/2000 |

OTHER PUBLICATIONS

Koga, K. et al. "In vitro and in situ evidence for the contribution of Labrasol and Gelucire 44/14 on transport of cephalexin and cefoperazone by rat intestine", Eur. J. Pharm. Biopharm. Nov. 2002 54(3): 311-8.

Koga, K., et al. "In vitro and in situ evidence for the contribution of Labrasol and Gelucire 44/14 on transport of cephalexin and cefoperazone by rat interstine", Eur. J. Pharm. Biopharm., Nov. 2002 54(3):311-8.

International Journal of Pharmaceutics, 106:15-23 (1994), "Self-emulsifying drug delivery systems (SEDDS) with Polyglycolized Glycerides for improving in vitro dissolution and oral absorption of lipophilic drugs".

(Continued)

*Primary Examiner* — Michael G Hartley
*Assistant Examiner* — Robert Cabral
(74) *Attorney, Agent, or Firm* — William E. Beaumont (57) ABSTRACT

The invention relates to an oral pharmaceutical composition of isotretinoin at least two excipients, one of the excipients being a hydrophilic excipient having an HLB value greater than or equal to 10 and the other excipient being an oily vehicle. The oral pharmaceutical composition is substantially devoid of food effect as characterized by a dissolution profile wherein at least 70% of the oral pharmaceutical composition is dissolved after about four hours in a USP2 dissolution apparatus at a paddle speed of 100 rpm, and a dissolution media composed of 900 mL of pH 7.5 buffer containing 0.11% pancreatin, 4.7% cholic acid, 0.14% sodium dihydroxide phosphate and 0.5% sodium hydroxide at 37° C.

14 Claims, 5 Drawing Sheets

(56) References Cited

OTHER PUBLICATIONS

Nankervis, et al. "Intestinal lymphotic transport of three retinoids in the rat after oral administration:effect of lipophilicity and lipid vehicle", International Journal of Pharmaceutics, 130:57-64 (1996).
"Effect of Lipid Vehicle on the intestinal lymphatic transport of isotretinoin in the rat", International Journal of Pharmaceutics, 119:173-181 (1995).
Constantinides, "Lipid microemulsions for improving drug dissolution and oral absorption: Physical and Biopharmaceutical Aspects", Pharmaceutical Resarch, vol. 12 No. 11 (1995).
Gershanik, "Self-dispersing lipid formulations for improving oral absorption of lipophilic drugs", Eur. Journal of Pharmaceuticals & Biopharm., 50:179-188 (2000).

* cited by examiner

PHARMACEUTICAL SEMI-SOLID COMPOSITION OF ISOTRETINOIN

FIELD OF THE INVENTION

The present invention relates to an oral pharmaceutical composition of isotretinoin containing at least two excipients, one of them being hydrophilic (i.e. having an HLB value superior or equal to 10), and the other being an oily vehicle.

BACKGROUND OF THE INVENTION

Isotretinoin (13-cis retinoic acid or 13-cis vitamin A), its isomers and some of its analogs are widely known to have therapeutic activity in the treatment of several severe skin disorders including cystic acne, hypertrophic lupus erythematosus, and keratinization disorders. Some evidence exists supporting the activity of isotretinoin in basal cell carcinoma and squamous cell carcinoma.

Unfortunately, isotretinoin is also a highly toxic drug. Indeed, although isotretinoin, which is a cis derivative, is known to be less toxic than all trans vitamin A derivatives, side effects resulting from its use such as headache, vomiting, irritation of mucosa and liver toxicity, occur frequently. Furthermore, isotretinoin is known to be highly teratogenic in both animals and humans.

In order to well understand the objectives and advantages of this invention, it is important to briefly summarize the physico-chemical pharmacokinetic properties of isotretinoin. Isotretinoin is a reddish-orange powder that is decomposed in the presence of light and atmospheric oxygen. Isotretinoin is poorly soluble in water, which results in its bioavailability being quite low after an oral intake (25% in fasted conditions and 40% in fed conditions). The maximum concentration ($C_{max}$) is reached after 24 hours, while the ($C_{max}$) of the active metabolite, 4-oxo-isotretinoin is reached after 6 hours. The elimination half-life of isotretinoin is of 7 to 37 hours while the half-life ($t_{1/2}$) of the active metabolite is of 11 to 50 hours. The steady-state concentrations of isotretinoin are reached after 1 week of treatment.

Very few publications and/or patents about the pharmaceutical formulation of isotretinoin are available. The drug is available on most markets under the form of a soft gelatin capsule containing a fatty liquid formulation of isotretinoin.

U.S. Pat. No. 4,464,394 describes for the first time the therapeutic use of isotretinoin and also briefly describes compositions of isotretinoin. The compositions involve the use of an antioxidant agent and of a carrier like lactose, starches or polyethylene glycols.

EP 0184942 describes more specific compositions of isotretinoin involving the use of an antioxidant, a chelating agent, a pharmaceutical carrier and a suspending agent. The composition obtained is described as being stable over time.

U.S. Pat. No. 4,545,977 relates to improved compositions of isotretinoin wherein taurine is associated with isotretinoin to reduce the drug's side effects.

U.S. Pat. No. 5,716,928 describes a method for increasing bioavailability and for reducing inter and intra individual variability of an orally administered hydrophobic pharmaceutical compound. The method includes orally administering the pharmaceutical compound with an essential oil or essential oil component in an amount sufficient to provide greater bioavailability of the active ingredient.

U.S. Pat. No. 6,028,054 relates to a method for increasing bioavailability of an orally administered hydrophobic pharmaceutical compound to humans. The method includes orally administering the pharmaceutical compound concurrently with a bioenhancer comprising an inhibitor of an cytochrome P450 3A enzyme or an inhibitor of P-glycoprotein mediated membrane transport.

U.S. Pat. No. 5,993,858 describes a self-microemulsifying excipient formulation for increasing the bioavailability of a drug which includes an emulsion including an oil or other lipid material, a surfactant and an hydrophilic co-surfactant.

It is believed that the prior art does not disclose a composition of isotretinoin containing at least two lipid materials, one of them being hydrophilic. The said composition may be a suspension, emulsion or microemulsion.

SUMMARY OF THE INVENTION

The advent of high throughput combinatorial chemistry and efficient receptor based in vitro activity screening has resulted in molecules with poor physicochemical properties (e.g., dissolution) for absorption across the gastrointestinal tract, like isotretinoin.

It is increasingly being recognized by the pharmaceutical industry that for these molecules drug delivery systems play an important role for improving oral bioavailability.

Although the process of passive diffusion is responsible for absorption of non ionized lipophilic molecules via the transcellular pathway, specialized absorption mechanisms, first-pass metabolisms and efflux systems at the gastrointestinal wall appear to play a major role in the lack of absorption and poor bioavailability for some molecules.

Isotretinoin is characterized by a low absolute bioavailability and a high inter and intra individual variability. Isotretinoin also presents a wide range of side effects among which some are severe (e.g., ocular, skin anemia, hepatic). It is consequently of particular interest to provide a reliable, stable and highly bioavailable formulation of isotretinoin.

Isotretinoin drug products marketed in the US before November 2012 all exhibit a significant food effect as described in their product monographs and measured by in-vivo pharmacokinetic analysis. The present invention is related to a pharmaceutical composition comprising isotretinoin which does not exhibit significant food effect as determined in vivo by pharmacokinetic studies and in vitro by dissolution in 900 mL of pH 7.5 Buffer containing 0.11% of pancreatin, 4.7% cholic acid, 0.14% sodium dihydrogen phosphate, and 0.5% sodium hydroxide using a USP Apparatus #2 (paddles), at 100 rpm and 37° C. For the purpose of the present invention, the term "food effect" is defined as a significant difference in maximum concentration, as determined by Area Under the Curve, when an oral drug product is taken with or without food.

Several possibilities are available to the formulator to increase the bioavailability of active ingredients (Table A).

TABLE A

| Option | Formulation technique |
|---|---|
| I | Use of salts, polymorphs. Precursors of the active molecule (=prodrugs) |
| II | Reduction of the particles' size of the active principle and of the excipients used (by trituration, grinding, micronization, precipitation controlled by solvent, temperature or ultrasonics). |
| III | Solid dispersions: Eutectic mixes Solid solutions Vitreous solutions |
| IV | Recrystallization in an aqueous solution of a surfactant |

TABLE A-continued

| Option | Formulation technique |
| --- | --- |
| V | Modification of the microenvironment:<br>Hydrophilization<br>pH (acidification) |
| VI | Incorporation of the active principle to lipidic systems |

It has been found that a semi-solid dosage form containing isotretinoin was advantageous for obtaining a good bioavailability of the isotretinoin. A semi-solid dosage form containing isotretinoin is a form in which isotretinoin is mixed with suitable melted excipients. The molten mix is then filled, for example, into hard gelatin capsules or other pharmaceutically acceptable capsules. At ambient temperature (temperature for example of less than 20° C.), the content of the capsule is a solid while at a temperature higher than 20° C. (for example at a temperature greater than or equal to 30° C., advantageously greater or equal to 35° C., preferably substantially at body temperature +/−37° C.), it is a liquid or semi-solid (paste). The isotretinoin may be solubilized in the mix of excipients or partially solubilized. The active ingredient may also be formulated as a suspension, emulsion or microemulsion.

Various lipidic excipients are available to the formulator to obtain a semi-solid formulation. Excipients compatible with hard gelatin capsule shells are: lipophilic liquid vehicles (refined specialty oils, medium-chain triglycerides and related esters), semi-solid lipophilic vehicles, solubilizing agents, emulsifying agents and absorption enhancers. The classification of fatty excipients is based on the hydrophilicity or lipophilicity of the excipients, characterized by the hydrophilic/lipophilic balance value (HLB). Examples of lipophilic excipients are vegetable oils (e.g., peanut oil, olive oil, soyabean oil, etc.) fatty acids (e.g., stearic acid, palmitic acid, etc.) fatty alcohols, etc. Examples of hydrophilic excipients are polyethylene glycol (PEG) with a molecular weight of greater than 3,000. Examples of amphiphilic (i.e., having lipophilic and hydrophilic properties) excipients are Poloxamers, Lecithin, PEG esters (Gelucire®), etc.

There are numerous advantages of the semi-solid formulations of isotretinoin of the present invention including: protection of the active ingredient from air and humidity, potential to increase the dissolution rate of the drug and hence its bioavailability, reducing the risk of the operator making the formulation being exposed to isotretinoin, reducing the risk of cross contamination, no possibility of demixing under the effect of vibrational mixing during the manufacturing process, and the facility of the production process.

The choice of the nature of the formulation influences the stability of the pharmaceutical formulation and the bioavailability of the isotretinoin contained in it. Generally, a maximum bioavailability is achieved by preparing and keeping the drug in the amorphous/solubilized state in a solid dispersion or in a lipid-based formulation. For these systems, the obstacle to dissolution that we are avoiding is significant "washing out" of the compound from solution into an insoluble crystalline form during the dissolution/release step in vivo.

These systems may consist of suspension, emulsion, microemulsion, self-emulsifying drug delivery systems (SEDDS®) or self-emulsifying microemulsion drug delivery system (SMEDDS®).

Microemulsions have the added advantage over suspensions, such as emulsions and dispersions, since thermodynamically they are more stable, they can be manufactured with little energy input and have generally a longer shelf-life. Nevertheless, a microemulsion formulation is not a guarantee of higher bioavailability in comparison to a suspension, as described hereafter.

The formation of oil-in-water (O/W) and water-in-oil (W/O) micro emulsions usually involves a combination of 3-5 basic compounds i.e. oil, surfactant, co-surfactant, water and electrolytes. The challenge is to select, for a particular application, oil(s) and surfactant(s) that are acceptable from a toxicological perspective and that provide a high bioavailability of the drug, i.e. isotretinoin.

The assessment of the quality of semi-solid lipid based formulations is quite difficult since the in vitro dissolution test is of little help. Indeed, the in vitro/in vivo correlation between dissolution and bioavailability is very poor for this kind of formulation. Other analytical tools are available to the formulator to try to predict the in vivo bioavailability of isotretinoin from various formulations, including the CACO-2 cells model, assessment of the percentage of drug dissolved in the formulation, differential scanning calorimetry, microscopy, etc.

Nevertheless, none of these analytical tools present a guarantee of in vitro/in vivo correlation and ultimately only pharmacokinetic studies on human subjects are reliable to assess the bioavailability of the drug.

DESCRIPTION OF THE PREFERRED EMBODIMENTS

The pharmaceutical composition of the invention is an oral semi-solid pharmaceutical composition of isotretinoin containing two lipidic excipients, one of them being hydrophilic and the other being an oily vehicle. The hydrophilic excipient has a HLB value of at least 10, for example equal to 10, but preferably greater than 10, such as greater or equal to 12, for example between 12 and 14.

The pharmaceutical composition of the invention contains advantageously at least one hydrophilic excipient with a HLB value of at least 10 selected from the group consisting of glyceroyl macrogolglycerides, polyethyleneglycol derivatives, and mixtures thereof. Preferably, the pharmaceutical composition contains from 20 to 80% by weight of a hydrophilic excipient with a HLB value of at least 10 selected from the group consisting of glyceroyl macrogolglycerides, polyethyleneglycol derivatives, and mixtures thereof.

The oily vehicle is selected from the group consisting of vegetable oils, medium chain triglycerides, fatty acid esters, amphiphilic oil, glycerol oleate derivative, and mixtures thereof. For example, the composition may contain from 5 to 70% by weight of an oily vehicle selected from the group consisting of vegetable oils, medium chain triglycerides, fatty acid esters, amphiphilic oil, glycerol oleate derivative, and mixtures thereof.

According to another detail of preferred pharmaceutical compositions of the invention, the composition further contains at least one surfactant, preferably selected from the group consisting of sorbitan fatty acid esters, polysorbate derivatives, polyoxyethylene sorbitan fatty acid esters, sodium laurylsulphate, derivatives of lecithine, propylene glycol esters, fatty acid esters of propylene glycol, fatty acid esters of glycerol, polyethylene glycol, and mixtures thereof. For example, the composition contains from 1 to 10% by weight of at least one surfactant.

Furthermore, the pharmaceutical formulation of the invention contains advantageously at least one disintegrant, preferably selected from the group consisting of povidone derivative, sodium croscarmellose and mixtures thereof.

The pharmaceutical composition of the invention may contain one or more surfactants and/or one or more disintegrants, but contains preferably one or more compounds acting as surfactants and one or more compounds acting as disintegrants.

The invention relates also to a pharmaceutical acceptable capsule containing at least one semi-solid composition of the invention, for example at least one composition of the invention as disclosed above. The capsule is for example selected from the group consisting of hard gelatin capsules, soft gelatin capsules, hypromellose capsules, and starch capsules.

The invention also relates to an oral pharmaceutical composition comprising isotretinoin, wherein said oral pharmaceutical composition is substantially devoid of food effect as characterized by a dissolution profile wherein at least 70% of the oral pharmaceutical composition is dissolved after about four hours in a USP2 dissolution apparatus at a paddle speed of 100 rpm, and a dissolution media composed of 900 mL of pH 7.5 buffer containing 0.11% pancreatin, 4.7% cholic acid, 0.14% sodium dihydroxide phosphate and 0.5% sodium hydroxide at 37° C.

The dissolution test method of the present invention is carried out in 900 mL of pH 7.5 Buffer containing 0.11% of pancreatin, 4.7% cholic acid, 0.14% sodium dihydrogen phosphate, and 0.5% sodium hydroxide using USP Apparatus #2 (paddles), at 100 rpm and 37° C. Dissolution samples are taken after 4 hours, and diluted to 50% with acetonitrile. Any USP-acceptable dissolution equipment may be used. Preferably, a USP dissolution apparatus #2 or #3 is used. More preferably, a USP #2 (paddle) dissolution apparatus equipped with 900 mL round bottomed and/or peak vessel flasks is used.

To ensure the pharmaceutical composition remains surrounded by the dissolution media, sinkers can be used with any dosage form that floats in the dissolution media. A small, non-reactive wire helix may be attached to the dosage form to keep it at the bottom of the vessel. Preferred sinkers include the Sotax® sinker, basket sinker, pronger sinker, O-ring, or spiral sinker. More preferred sinkers include the Japanese Pharmacopeia basket sinkers.

The pH of the media may vary from 2.0 to 12.0, preferably from 4.0 to 8.0, and more preferably from 7.0 to 8.0. The buffer of the media may be comprised of phthalate, phosphate, barate, and/or acetate, and will depend on the final pH value. Sodium dihydrogen phosphate is the preferred buffer. Pancreatin is added to the media to destroy any gelatin crosslinking.

Cholic acid is added to increase the solubilization of isotretinoin. The amount may vary from 0.1% to 0.6%, preferably from 0.3% to 0.4%.

For determining the amount of the isotretinoin in the samples after 4 hours of dissolution, any validated analytical method may be used, including UV spectrophotometry, colorimetry, HPLC, or capillary electrophorese. The preferred analytical method is HPLC equipped with a UV detector of 353 mm and $C_{18}$ column, for example, LiCrospher® 100 RP-18 end capped, with a flow rate of 2.0 mL/min of mobile phase consisting of acetonitrile:water:glacial acetic acid (85:15:0.5) at a temperature of 40° C.

EXAMPLES

The present invention will now be illustrated by certain examples which are provided solely for purposes of illustration and are not intended to be limitative.

The present invention relates to a semi-solid formulation of isotretinoin containing at least 2 lipidic excipients, one of them being a hydrophilic excipient (having a high HLB value, namely >10) and the other an oily excipient. The molten mix of these two excipients allows total or partial (depending on the ratio between excipients) dissolution of the isotretinoin. Different kinds of formulations (SEDDS® or suspensions) of isotretinoin have been formulated. For suspensions, it was possible to dissolve a high fraction of isotretinoin in the mix of excipients and even the whole quantity of the active ingredient if the manufacturing conditions (high temperature and long time of mixing) and the formulations were optimized. Excipients particularly suitable for the dissolution of isotretinoin were lauroyl Macrogol-32 glycerides (Gelucire® 44/14, Gattefossé) and Stearoyl Macrogol-32 glycerides (Gelucire® 50/13, Gattefossé). When those hydrophilic components are melted together with an oily vehicle, it allows obtaining very stable suspensions of isotretinoin in which an important part of the active ingredient is dissolved. A surfactant may also be added to the formulation to further improve the physical stability of the suspension.

SEDDS® formulations of isotretinoin are also stable and may give an improved bioavailability of the drug.

Figure 1:
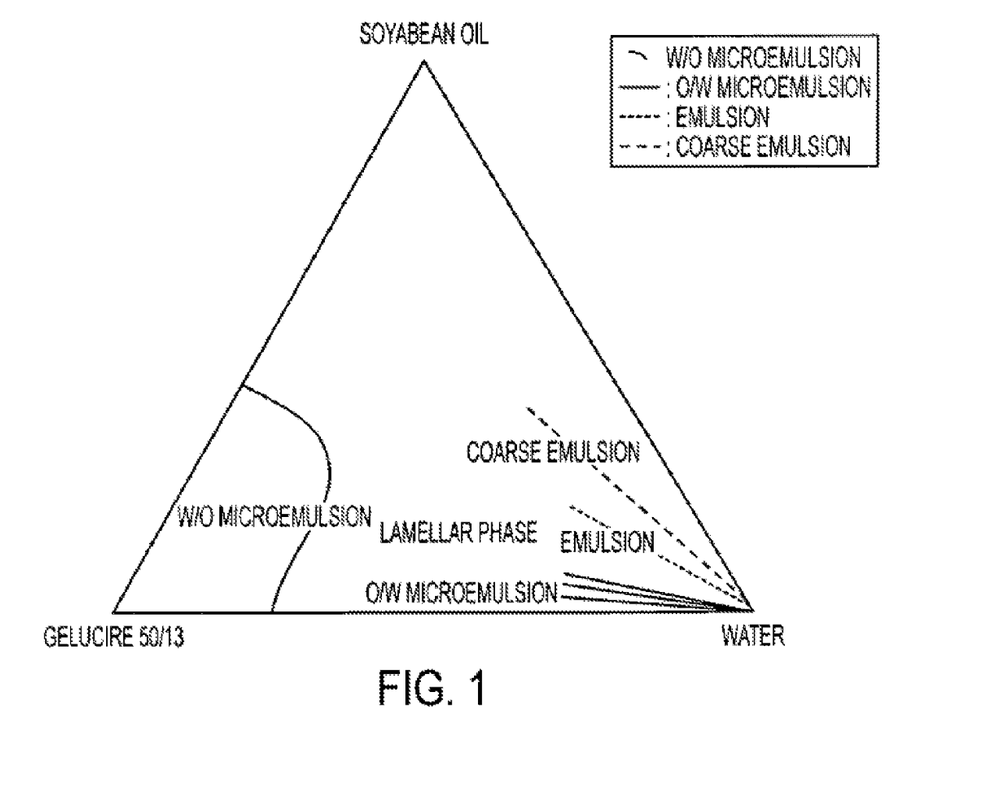
FIG. 1 is a ternary diagram of a formulation containing only Gelucire® 50/13 and soybean oil, the third component being water.

Ternary diagrams illustrate the different areas corresponding to different physical states, namely, coarse emulsion, true emulsion, lamellar solution or micellar solution, as the ratio between excipients is varied. The behavior of the formulation in the presence of water changes when the ratio changes. One example of this ternary diagram is given in FIG. 1 for a formulation of isotretinoin containing Gelucire® 50/13 and soybean oil.

Example 1

Effect of Different Lipophilic Compounds

The effect of different lipophilic excipients was evaluated in the dosage form of semi-solid capsules. The semi-solid capsules were made by addition of the active substance to the pre-melted lipophilic compounds followed by the filling of the liquid into hard gelatin capsule.

The active substance was incorporated into formulations, listed in table 1, consisting of glyceroyl macrogolglyceride associated with soybean oil or derivative, medium chain triglyceride.

TABLE I

| Formulations number | 1 | 2 | 3 | 4 | 5 |
|---|---|---|---|---|---|
| Isotretinoin | 20 | 20 | 20 | 20 | 20 |
| Labrafil ® M1944 CS | 132 | | | | |
| Gelucire ® 50/02 | 198 | 93 | | | |
| Gelucire ® 44/14 | | 217 | | | |
| Gelucire ® 50/13 | | | 76 | 60 | 60 |
| Soybean oil | | | 304 | 320 | |
| Mygliol ® | | | | | 320 |

The use of stearoyl macroglyceride (Gelucire® 50/13, Gattefosse) and soybean oil allows provides a formulation with a dissolution profile similar to the reference (Roaccutane® 20 mg, Roche).

The formulations with Labrafil® or Gelucire® 50/02 are too lipophilic to give a good dissolution in water.

In general, the use of an oily excipient can improve the absorption of a lipophilic drug by increasing the solubility of the drug in the lipidic phase, but the release of the active ingredient from the formulation can be slowed down due to the high affinity of the lipophilic drug for the oily phase.

The use of dispersed systems (emulsions or suspensions) instead of only lipophilic or hydrophilic vehicles, improves the absorption of the drug as well as increasing a larger contact surface.

Concerning the Gelucire®, the process of drug release varies according to the HLB of the excipient. Gelucire® with high HLB values were found to be the most favorable for a rapid release of the drug (by diffusion and erosion).

The drug release profiles of Formulations 1 to 5 were evaluated in phosphate buffer pH 7.5 with laurylsulfate and pancreatin. The percent of isotretinoin released after 4 hours is given in the following table II.

TABLE II

| | Percent of isotretinoin released after 4 hours | | | | |
|---|---|---|---|---|---|
| Formulations Number | 1 | 2 | 3 | 4 | 5 |
| % released | 20.1 | 69.1 | 46.0 | 60.3 | 78.1 |

The percent of isotretinoin released from the reference (Roaccutane® 20 mg) after 4 hours is 55.37%.

Example 2

Influence of the Ratio Oily Vehicle/Surfactive Agent on the Dissolution and Absorption of the Formulation The study of the ratio of oily vehicle/surfactive agent with the construction of a ternary diagram gives information on the dissolution profile of the formulation in water.

Stearoyl macrogolglyceride (Gelucire® 50/13), which is known to be a drug solubilizer and emulsifying agent of different drugs (in SMEDDS® or SEDDS®), was tested in association with soybean oil.

This component has the ability to solubilize a great part of isotretinoin in the formulation. This data is listed in table III.

TABLE III

| Formulations number | 1 | 2 | 3 | 4 | 5 | 6 |
|---|---|---|---|---|---|---|
| Isotretinoin | 20 | 10 | 10 | 20 | 20 | 20 |
| Soybean oil | 270 | 135 | 40 | 152 | 57 | 133 |
| Gelucire ® 50/13 | 84 | 42 | 200 | 228 | 323 | 247 |
| Filling weight | 374 | 187 | 260 | 400 | 400 | 400 |
| Ratio oil/Gelucire ® 50/13 | 3.2 | 3.2 | 0.2 | 0.67 | 0.17 | 0.54 |

In the presence of water, the behavior of these formulations are different

Formulations 1 and 2: formation of coarse emulsion with large droplet sizes

Formulations 3 and 5: formation of micellar phase or microemulsion

Formulations 4 and 6: formation of emulsion with homogeneous droplet size The percentage of isotretinoin released increases generally with the percentage of Gelucire® in the formulation (increased solubility of the active in this vehicle). For Formulation 1 (ratio oil/Gelucire® 50/13=3.2) 54.9% released after 4 hours and for Formulation 3 (ratio oil/Gelucire® 50/13: 0.2), 91.2% released after 4 hours.

Dissolution Test

For poorly soluble molecules, the prediction power of the in vitro dissolution test is weak since the in vitro/in vivo correlation is known to be poor. Nevertheless, an optimized dissolution test (using enzymes and surfactant) is of some help to assess the rate of release of the drug from the lipidic composition. It must be noted that the conditions of the dissolution test (dissolution medium, speed of the paddles, temperature, etc.) influence the results of the test and should consequently be standardized to allow comparison between various formulations.

Figure 2:
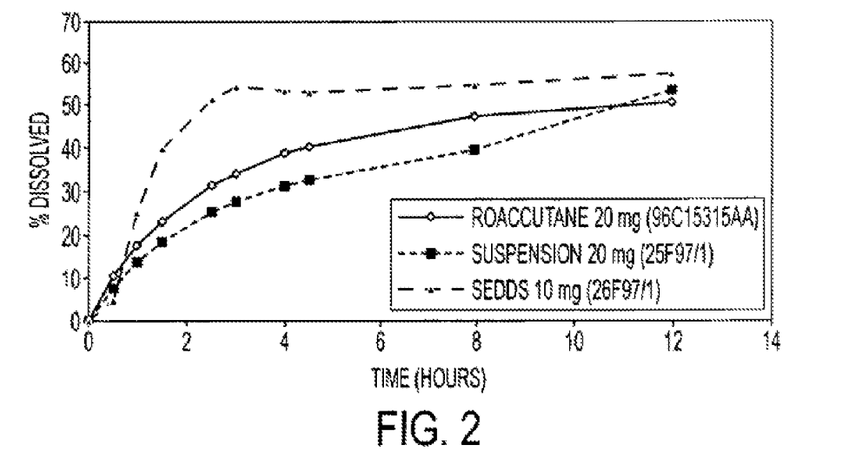
FIG. 2 shows the dissolution rate of a reference product (Roaccutane®-20 mg active agent), of a suspension containing 20 mg isotretinoin and of an emulsion SEDDS® containing 10 mg isotretinoin.

The conditions of the solution test used for assessing the dissolution of isotretinoin were the following
paddle apparatus
150 rpm
37° C.
buffer pH 7.5 with laurylsulfate 2.5% and pancreatin 1 g/L FIG. 2 shows the dissolution rate of a reference product (Roaccutane®—20 mg active agent), of a suspension containing 20 mg Isotretinoin and of an emulsion SEDDS® containing 10 mg Isotretinoin (formulation given below).

As the information provided by the dissolution test is poor in terms of correlation with in vivo bioavailability, it is of interest to dispose of other means to predict the in vivo bioavailability.

The caco-2 cell culture system can be used for determining permeability of compounds (especially for poorly soluble compounds). The caco-2 cell model allows one to measure the transport of drug from the apical to the serosal side as well as from the serosal to the apical side. This gives the ability to determine if an efflux system is operational.

The caco-2 cells model is interesting because:
 (a) The cells used are from human origin (contrary to the models using segments of animal guts). The cells are from an adenocarcinoma of the human colon but spontaneously differentiate into small intestine's epithelial cells. When put in culture, the cells form a monolayer of polarized cells expressing several enzymatic systems.
 (b) The model offers a better prediction of the human intestine absorption than do animal models.
 (c) The reproducibility of the test is relatively high.
 (d) The model allows one to take samples from both apical and basolateral sides.

As described below, Caco-2 cells experiments have been performed with one SEDDS® and one suspension isotretinoin formulation.

Results

It was first proven that neither the active ingredient nor the excipient used in the formulations were toxic to the cells. It was also proven that the integrity of the membranes of the cells was maintained during the entire experiment.

Methodology:

The formulations tested were put in solution in 250 ml of BME. Taurocholate (10 mM) was added to the solutions to better replicate the in vivo physiological conditions. The different solutions so prepared were put in contact with Caco-2 cells at the apical or basolateral side. The cells culture inserts were incubated for 3 hours at 37° C. and samples of 100 µl taken every hour for analysis.

The formulations tested were the following:

TABLE IV

|  | SEDDS ® 26F97/1 | Formulation Suspension 25F97/1 |
|---|---|---|
| Isotretinoin | 10 mg | 20 mg |
| Gelucire ® 50/13 | 134 mg | 83.7 mg |
| Phospholipon 90 ® | 11 mg | — |
| Tween 80 ® | 71 mg | — |
| IPP ® | 24 mg | — |
| Soybean oil | — | 270 mg |
| Gelatin Capsule | 1 | 1 |

Results

Passage of Formulations from Apical Side→Basolateral Side

TABLE V

| Time minutes | SEDDS ® (26F97/1) | Suspension (25F97/1) | SEDDS ® + TC | Suspension + TC | Control |
|---|---|---|---|---|---|
| 60 | 0.7721 | 0.6708 | 0.7019 | 0.6469 | 0.0718 |
| 120 | 2.4096 | 0.8749 | 1.4347 | 0.9513 | 0.1836 |
| 180 | 2.6226 | 1.1311 | 3.2419 | 1.5073 | 0.6156 |

Passage of Formulations from Basolateral Side→Apical Side

TABLE VI

| Time minutes | SEDDS ® (26F97/1) | Suspension (25F97/1) | SEDDS ® + TC | Suspension + TC | Control |
|---|---|---|---|---|---|
| 60 | 2.0496 | 0.3948 | 8.1291 | 0.8713 | 0.0650 |
| 120 | 3.0844 | 0.9068 | 8.3496 | 1.8460 | 0.1131 |
| 180 | 4.3653 | 1.0763 | 9.7110 | 2.0779 | 0.1481 |

The results demonstrate that the passage of isotretinoin is superior for the SEDDS® formulation than for the suspension formulation. In order to confirm these results, a comparative pharmacokinetics study has been performed.

PK Studies

The bioavailability of SEDDS® (26F9711) and suspension (25F9711) isotretinoin formulations has been assessed and compared to the bioavailability of the reference (Roaccutane® 20 mg, Hoffman La Roche) on six healthy volunteers in a single dose, three way, cross-over pharmacokinetic study). The drug was taken with food (Europeanbreakfast). The plasma concentration of isotretinoin and its active metabolite 4-oxo-isotretinoin were quantified using a fully validated LC/MS/MS method.

Figure 3:
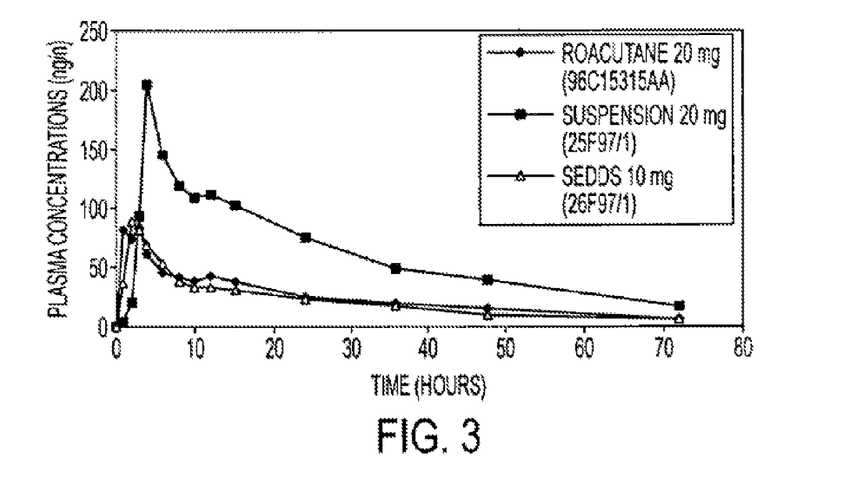
FIG. 3 shows an in vivo comparative pharmacokinetic profile of isotretinoin.

FIG. 3 describes the mean pharmacokinetic profile obtained for each formulation.

The following TABLE VII gives the value of the main pharmacokinetics parameters obtained for each formulation of isotretinoin.

| Formulations | $AUC_{72h}$ (ng · h/ml) | $C_{max}$ (ng/ml) | $T_{max}$ (h) |
|---|---|---|---|
| Roaccutane ® 20 mg (96C15315AA) | 1747.89 | 116.63 | 1.83 |
| Suspension 20 mg (25F97/1) | 4308.72 | 230.96 | 5.67 |
| SEDDS ®'10 mg (26F97/1) | 1494.64 | 98.36 | 3.00 |

It appears that both the SEDDS® and the suspension formulations are able to significantly increase the bioavailability of isotretinoin in comparison to the marketed reference product. Indeed the ratio between $AUC_{72h}$ of the suspension 20 mg and Roaccutane® 20 mg is of 2.47. The SEDDS® 10 mg present an $AUC_{72h}$ similar to that of Roaccutane® 20 mg what means an approximately 2-fold increase of bioavailability (ratio $AUC_{72h}$ SEDDS® 10 mg/$AUC_{72h}$ Roaccutane® 20 mg=0.86). Furthermore, the suspension and SEDDS® formulations both presented a lower intra-individual variability of the bioavailability as demonstrated by the values of relative standard deviations (rsd) which are of 36.0%, 22.72% and 28.18% for Roaccutane® 20 mg, suspension 20 mg and SEDDS® 10 mg, respectively.

Nevertheless, the results obtained in vivo are not correlated with the results obtained on caco-2 cells since with this model the permeability of the SEDDS® formulation was much higher than the permeability of the suspension formulation. In contrast, in the in vivo testing the suspension formulation gave the best results.

A second pharmacokinetic study was performed on completely different formulations (6 subjects, 2-way, fed, crossover study). Specifically, in the second pharmacokinetic study the formulations of isotretinoin under the form of a suspension in which the ratio Gelucire® 50/13 and soybean oil was very different from the suspension formulation used in the first pharmacokinetic study.

The two formulations tested are listed in Table VIII.

TABLE VIII

| Batch number | H23K99/1 | H07L99/1 |
|---|---|---|
| Isotretinoin | 20 | 20 |
| Gelucire ®50/13 | 247 | 240 |
| Soyabean oil | 133 | 130 |
| Span 80 ® | — | 20 |

Figure 4:
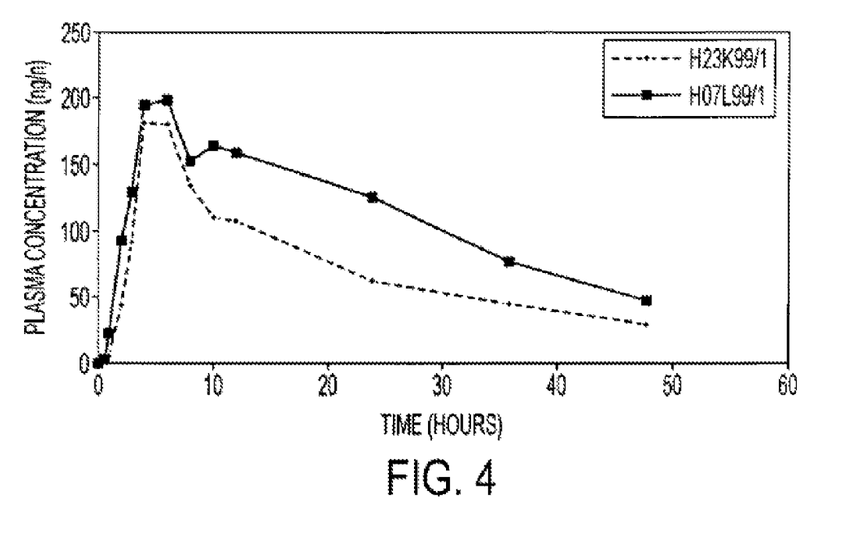
FIG. 4 shows comparative pharmacokinetic profiles of isotretinoin.

FIG. 4 provides the comparative pharmacokinetic profiles of the isotretinoin formulations of Table VIII.

Figure 5:
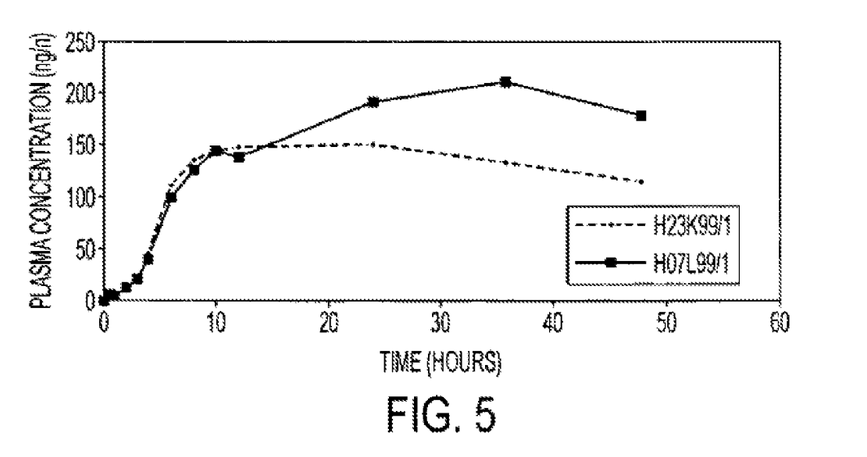
FIG. 5 shows comparative pharmacokinetic profiles of different formulations for 4-oxo-isotretinoin, the active metabolite of isotretinoin.

FIG. 5 provides the comparative pharmacokinetic profiles of the isotretinoin formulations of Table VIII for 4-oxo-isotretinoin, the active metabolite of isotretinoin.

In order to confirm the first bioavailability data obtained with the present invention, a larger pharmacokinetic study has been performed. The bioavailability of a capsule of isotretinoin 16 mg (see Table IX below for the formulation) according to the present invention has been assessed and compared to the bioavailability of the reference (ROACCUTANE® 20 mg capsule, Roche) on 24 healthy subjects.

This study (SMB-ISO-SD011) was a single dose, two treatment, two period, two sequence, randomized, crossover design with at least 18 days wash-out between the two periods.

The subjects were healthy Caucasian volunteers of both sexes (non-pregnant, non-breast-feeding), aged 18 to 50 years, non-smokers or smoking less than 10 cigarettes per day.

The drug was taken with food (a European breakfast).

Blood samples were collected according to the following sampling schedule: pre dose and 1 h, 2 h, 3 h, 4 h, 5 h, 6 h, 7 h, 8 h, 10 h, 12 h, 14 h, 24 h, 36 h, 48 h, 72 h, 96 h, 120 h, 168 h and 216 hours post-dose.

The plasma concentration of isotretinoin and its active metabolite, 4-oxo-isotretinoin, were quantified using a fully validated LC/MS/MS method. The continuous variables were evaluated according to a univariate ANOVA, based on log-transformed data. The Wilcoxon non-parametric ANOVA were used where appropriate. Bioequivalence was evaluated using the Shuirman two one-sided t-test (90% C1) and the Westlake single sided confidence interval (95% CL).

Figure 6:
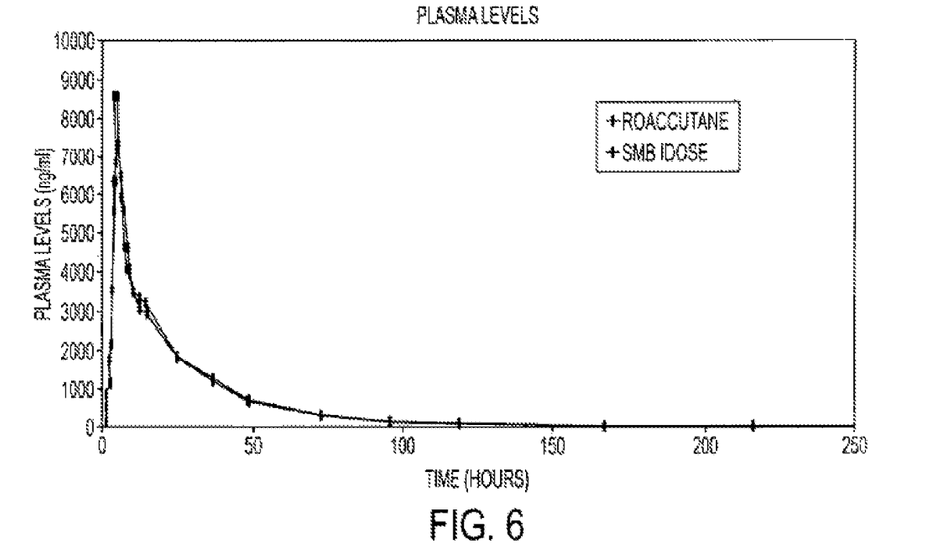
FIGS. 6 and 7 illustrate the mean pharmacokinetic profiles of isotretinoin and 4-oxo-isotretinoin for two formulations.
Figure 7:
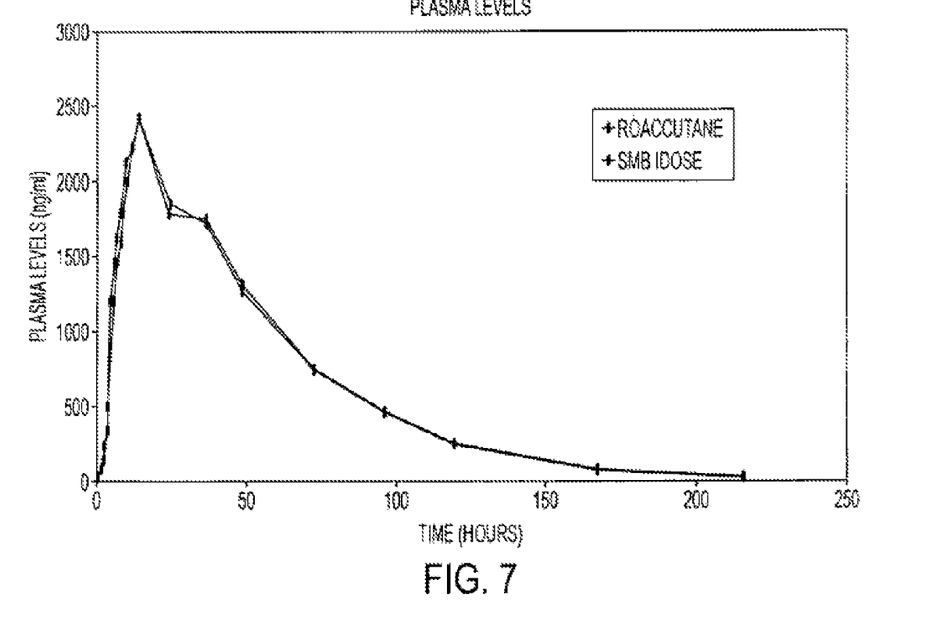

FIGS. 6 and 7 describe the mean pharmacokinetic profile of isotretinoin and 4-oxo-isotretinoin for the two formulations (n=24 subjects) while the Tables X and XI provide the comparative, main pharmacokinetic parameters.

TABLE IX

| Formulation of isotretinoin 16 mg (mg/capsule) | |
| --- | --- |
| Isotretinoin | 16 |
| Stearoyl macrogol glycerides (Gelucire 50/13 ®) | 192 |
| soybean oil refined | 104 |
| sorbitane oleate (Span 80'") | 16 |

As seen below, the dose of 16 mg of the formulation corresponding to the present invention gives a bioavailability similar to 20 mg of the marketed formulation, which provides evidence of the supra-bioavailability of the formulation corresponding to the present invention.

Table X and XI provide the value of the main pharmacokinetics results and statistical analysis obtained for each formulation (i.e., ROCCUTANE® 20 mg and isotretinoin 16 mg) of isotretinoin and 4-oxoisotretinoin.

This study demonstrated that ROACCUTANE® 20 mg and isotretinoin 16 mg are bioequivalent after a single oral dose administration of each product in fed conditions. Indeed, the primary parameters AUC (AUC∞ and $AUC_{216h}$) were within the predetermined confidence interval.

This study demonstrated also that Isotretinoin 16 mg according to the invention has a safety profile comparable to that described in the literature for other isotretinoin preparations and similar to that of ROACCUTANE®20 mg.

Pharmacokinetic Results and Statistical Analysis of Comparative Study in 24 Volunteers for Isotretinoin (Log-Transformed Data). (See Table X)

TABLE X

| | Bioequivalence tests/Isotretinoin Results | | | |
| --- | --- | --- | --- | --- |
| Parameter | ROACCUTANE 20 mg | Isotretinoin 16 mg | Shuirman 90% C1 Range | Westlake 95% CL |
| AUC∞ | 5657.09 (ng h/ml) | 5696.92 (ng h/ml) | 92-123 (h/ml) | 19.07 |
| ±SD | ±2682.98 | ±1938.89 | | |
| ±RSD | ±47.42 | ±34.03 | | |
| $AUC_{216h}$ | 5601.36 (ng h/ml) | 5664.39 (ng h/ml) | 92-124 | 19.51 |
| ±SD | ±2670.85 | ±1953.52 | | |
| ±RSD | ±47.68 | ±34.48 | | |

TABLE X-continued

| | Bioequivalence tests/Isotretinoin Results | | | |
| --- | --- | --- | --- | --- |
| Parameter | ROACCUTANE 20 mg | Isotretinoin 16 mg | Shuirman 90% C1 Range | Westlake 95% CL |
| $C_{max}$ | 386.68 (ng/ml) | 441.79 (ng/ml) | 103-140 | 28.81 |
| ±SD | ±218.21 | ±197.43 | | |
| ±RSD | ±56.43 | ±44.68 | | |
| $T_{max}$ | 4.92 (h) | 4.50 (h) | | |
| ±SD | ±2.22 | ±0.66 | | |
| ±RSD | ±45.24 | ±14.65 | | |

Pharmacokinetic results and statistical analysis of comparative study in 24 volunteers for 4-oxoisotretinoin (log-transformed data) (See Table XI)

TABLE XI

| | Bioequivalence tests/oxoisotretinoin Results | | | |
| --- | --- | --- | --- | --- |
| Parameter | ROACCUTANE ® 20 mg | Isotretinoin 16 mg | Shuirman 90% CI Range | Westlake 95% CL |
| AUC∞ | 5750.36 (ng h/ml) | 5769.04 (ng h/ml) | 92-124 (h/ml) | 19.65 |
| ±SD | ±2717.38 | ±2161.97 | | |
| ±RSD | ±47.26 | ±37.48 | | |
| $AUC_{216h}$ | 5638.32 (ng h/ml) | 5712.21 (ng h/ml) | 92-125 | 20.46 |
| ±SD | ±2704.73 | ±2126.61 | | |
| ±RSD | ±47.80 | ±37.23 | | |
| $C_{max}$ | 111.52 (ng/ml) | 115.15 (ng/ml) | 94-125 | 20.18 |
| ±SD | ±69.62 | ±66.25 | | |
| ±RSD | ±62.43 | ±57.53 | | |
| $T_{max}$ | 17.83 (h) | 16.33 (h) | | |
| ±SD | ±10.60 | ±10.11 | | |
| ±RSD | ±59.43 | ±61.88 | | |

Example 3

To study the effect and verify the capability of the dissolution test, containing cholic acid, to detect Isotretinoin containing formulations without food effect the following formulation was prepared, tested in dissolution and in vitro studies and compared to the commercially available product in the market (Accutane®). Gelatin capsules containing 20 mg of Isotretinoin were prepared as follows.

TABLE XII

| Ingredient | Amount [kg] |
| --- | --- |
| Isotretinoin USP | 2.224 |
| Stearyl Macrogol Glycerides | 26.7 |
| Soybean Oil, USP | 14.5 |
| Sorbitan Monooleate, NF | 2.22 |
| Propyl Gallate, NF | 0.00912 |

The pre-weighed amounts of stearyl macrogol glycerides, soybean oil, sorbitan monooleate, and propyl gallate were added in a double-jacketed stainless steel container equipped with a mixing device, and heated at a temperature between about 65° C. and about 85° C. When all excipients were molten, isotretinoin was added to the container while mixing. 410 mg of the molten blend was added into size #0 gelatin capsules, producing capsules containing 20 mg of isotretinoin.

Dissolution testing: A dissolution test using 6 capsules of the present example was performed. The dissolution test is performed in accordance with general rules of USP for dissolution testing A dissolution medium pH 7.5 [20 L] was prepared by introducing 27.6 g of sodium dihydrogen phosphate in an appropriate container and dissolving it with about 4 liters of water. Next, 12 liters of water were added. Thereafter, 380 mL of sodium hydroxide 6N were progressively added under stirring. If needed, the mixture was sonicated until all of the sodium dihydrogen phosphate is dissolved. 940 g of cholic acid was progressively added under stirring until totally dispersed. If necessary, small amounts of NaOH 6N were added until dissolved. Water was added to bring the total volume to about 20 L, mixed, and the pH was adjusted to 7.5 with NaOH if necessary. The exact amount of medium to be used was then removed, and 1 g of pancreatin per each 900 mL of medium was added and mixed.

The dissolution test parameters were: dissolution volume 900 mL; temperature 37° C.; paddle rotation speed 100 rpm; test time for sampling 4 hours; quantification HPLC/UV at 353 nm±4 nm.

Test: 900 mL of dissolution medium was slowly added to each dissolution vessel and heated at 37.0° C.±0.5° C. Paddles were lowered into the dissolution medium and the paddle rotation speed was set to 100 rpm. Each of the six capsules was inserted into a corresponding sinker, and one sinker containing one isotretinoin capsule was introduced into each dissolution vessel. Samples were taken (10.0 mL) in each dissolution vessel after 4 hours.

The solution was immediately filtered slowly through a 0.45 μm filter, and the first milliliters were discarded and introduced into a glass vial. The samples were further diluted by pipetting 5 mL of the sample and 5 mL of acetonitrile into a container.

Two milliliters of the diluted sample were mixed and transferred to a HPLC amber vial.

Analysis: The chromatographic conditions were: column LiCrospher® 100 RP-18 end capped (125×4 mm), 5 μm or equivalent; mobile phase acetonitrile:water:acetic acid glacial (85:15:0.5); flow rate 2.0 mL/min; temperature 40° C.; detection UV at λ 353 nm±4 nm; injection 80 μL; stop time 4 minutes.

To prepare the mobile phase (85:15:0.5 acetonitrile:water: acetic acid), 850 mL of acetonitrile, 150 mL of water, and 5.0 mL of acetic acid glacial were added to a one liter flask. The mix was then homogenized and degassed in an ultrasonic bath for 15 minutes before use.

Methylene Chloride Reagent: One liter of methylene chloride was added to 50 g of sodium bicarbonate. The solution is shaken and allowed to stand overnight. At the time of use, it is filtered and 10 mg of butylated hydroxytoluene are added for each mL of reagent.

The isotretinoin-containing formulation has a reduced food effect if the results obtained comply with the following specifications:

TABLE XIII

| Stage $S_1$ | Stage $S_2$ | Stage $S_3$ |
|---|---|---|
| Number of capsules n = 6 | Number of capsules n = 12 | Number of capsules n = 24 |
| Each of the 6 units is NLT 80% | Mean of 12 units NLT 75% All units are NLT 60% | Mean of 24 units NLT 75% NMT 2 units are LT 60% No unit is less than 50% |

Demonstration that the formulation should not have a significant food effect since the result obtained for 6 units was 92% dissolved. [limit for n=6 NLT 80%]

An open label, single dose, four-way, randomized crossover comparative bioavailability of two formulations of isotretinoin capsules in healthy volunteers under fed and fasting conditions was conducted with the same formulation: PRMI Study 2003-627.

The objective of the study was to evaluate the comparative bioavailability between Isotretinoin 2×20 mg capsules (Example 1) and Accutane® 40 mg capsules in healthy male and female volunteers under fasting and fed conditions.

Treatment A (Test): Isotretinoin 20 mg Capsules [40 mg administered after an overnight fast of at least 10 hours]

Treatment B (Test): Isotretinoin 20 mg Capsules [40 mg administered after a modified high fat, high calorie breakfast]

Treatment C (Test): Accutane® 40 mg Capsules, Lot No.: U0622; [40 mg administered after an overnight fast of at least 10 hours]

Treatment D (Test): Accutane® 40 mg Capsules, Lot No.: U0622; Expiration Date: 10-2004 [40 mg administered after a modified high fat, high calorie breakfast]

Sixty (60) (40 male and 20 female) subjects were dosed in Period 1, with 57 subjects completing the entire study.

Blood samples were obtained at −10, −2, 0, 1, 2, 2.5, 3, 3.5, 4, 4.5, 5, 5.5, 6, 7, 8, 10, 12, 14, 16, 20, 24, 36, 48, and 72 hours following drug administration.

Figure 8:
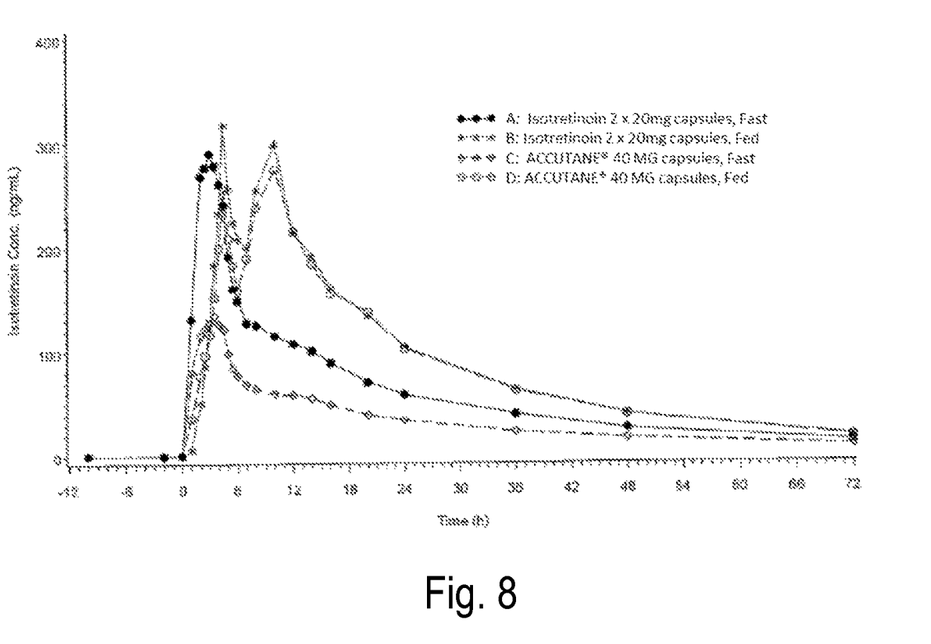
FIG. 8 shows in vivo comparative pharmacokinetic profiles of isotretinoin obtained after administration of 2×20 mg of the present invention versus 20 mg of a product in the market (Accutane®) taken with and without food.

No serious adverse events were reported during the study. The mean Isotretinoin plasma concentration versus time are shown in FIG. 8

TABLE XIV

Plasma Isotretinoin Results (n = 57)

| Parameter | Treatment Type | Trt | Arithmetic (CV %) | Geometric | Type | Code | Contrast Ratio (%) | 90% CI (%) | CV % |
|---|---|---|---|---|---|---|---|---|---|
| AUCi (mg · h/mL) | T - Fast | A | 4676.08 (28) | 4470.45 | T: Food Effect | B vs. A | 149.78 | 140.52-159.66 | 21 |
| | T - Fed | B | 6858.70 (21) | 6695.87 | R: Food Effect | D vs. C | 252.60 | 236.98-269.26 | |
| | R - Fast | C | 2619.26 (30) | 2500.01 | T/R - Fast | A vs. C | 178.82 | 167.76-190.60 | |
| | R - Fed | D | 6561.62 (26) | 6315.15 | T/R - Fed | B vs. D | 106.03 | 99.47-113.02 | |
| Cmax (mg/mL) | T - Fast | A | 347.00 (35) | 323.18 | T: Food Effect | B vs. A | 134.39 | 122.60-147.32 | 30 |
| | T - Fed | B | 466.43 (38) | 434.33 | R: Food Effect | D vs. C | 267.53 | 244.05-293.28 | |
| | R - Fast | C | 169.66 (29) | 161.43 | T/R - Fast | A vs. C | 200.20 | 182.63-219.46 | |
| | R - Fed | D | 471.32 (41) | 431.88 | T/R - Fed | B vs. D | 100.57 | 91.74-110.24 | |

T = Test
R = Reference

TABLE XV

Plasma 4-oxo-isotretinoin results (n = 57)

| Parameter | Treatment Type | Trt | Arithmetic (CV %) | Geometric | Type | Code | Contrast Ratio (%) | 90% CI (%) | CV % |
|---|---|---|---|---|---|---|---|---|---|
| AUCi | T - Fast | A | 12962.12 (43) | 11865.08 | T: Food Effect | B vs. A | 178.01 | 162.09-195.50 | 31 |
| (mg · h/mL) | T - Fed | B | 22080.03 (31) | 21121.13 | R: Food Effect | D vs. C | 312.59 | 284.63-343.30 | |
| | R - Fast | C | 6667.38 (46) | 6049.60 | T/R - Fast | A vs. C | 196.13 | 178.59-215.39 | |
| | R - Fed | D | 20485.24 (39) | 18910.45 | T/R - Fed | B vs. D | 111.69 | 101.70-122.66 | |
| Cmax | T - Fast | A | 177.23 (39) | 163.73 | T: Food Effect | B vs. A | 215.24 | 196.12-236.23 | 31 |
| (mg/mL) | T - Fed | B | 368.76 (28) | 352.42 | R: Food Effect | D vs. C | 439.82 | 400.75-482.71 | |
| | R - Fast | C | 75.61 (35) | 70.55 | T/R - Fast | A vs. C | 232.09 | 211.48-254.71 | |
| | R - Fed | D | 336.61 (38) | 310.28 | T/R - Fed | B vs. D | 113.58 | 103.49-124.65 | |

T = Test
R = Reference

The results of the pharmacokinetic study show that for Isotretinoin plasma levels as expressed by Area Under the Curve (AUC) and maximum concentration ($C_{max}$) (Table XVI) the formulation of Example 3 does not have a significant food effect.

TABLE XVI

Summary of Pharmacokinetic parameters
Isotretinoin plasma levels

| | AUCi | | | $C_{max}$ | | |
|---|---|---|---|---|---|---|
| | Present invention Example 3 | Product in the market | Ratio | Present invention Example 3 | Product in the market | Ratio |
| Fed | 6858 | 6561 | 105 | 466 | 471 | 99 |
| Fasted | 4676 | 2619 | 179 | 347 | 169 | 205 |

Dissolution Test

The need for a biorelevant dissolution method for isotretinoin compositions that may replace the costly biostudy by a dissolution test is of the utmost need for the pharmaceutical industry. Such a biorelevant dissolution method will permit one not only to assure the quality and performance of each and every lot produced but also will drastically reduce the cost and time needed each time a change is required during the lifespan of the product. Such a dissolution test also would be very valuable in the research and development phases of a project since it will permit formulators to distinguish between isotretinoin-containing formulations with and without food effect.

The United States Pharmacopeia (USP) is one well-known standard source of information which provides, among other things, for dissolution testing in the majority of monographs for such dosage forms.

Current USP dissolution methods most commonly employ a temperature programmable water bath, maintained at about 37° C., in which sample vessels are submerged. These vessels contain a predetermined volume of dissolution media and a means to agitate the contents of the vessel. This may be accomplished by means of a rotating basket attached to a shaft or with a paddle which is also attached to a shaft, both means are generally described in USP 23rd edition Chapter 711 (Dissolution) pages 1791-1793. The solid dosage form is placed into the media filled vessel at time zero and specific vessel temperature and mixing speeds are maintained. At fixed time intervals (e.g. 2, 4, 8 hours, etc.) a small aliquot of sample is taken from each vessel, usually by a multi channeled pumping system, and transported to either a cuvette or a sample vial for subsequent spectrophotometric or high pressure liquid chromatography (HPLC) analysis, respectively. Plotting percentage dissolution of a solid dosage form through time results in a dissolution profile.

As it relates to isotretinoin, the United States Pharmacopeia (USP 35) official Dec. 1, 2012 describes three test methods for the measurement of dissolution of isotretinoin capsules. Unfortunately, these methods do not sufficiently distinguish between isotretinoin formulations with and without food effect (table I FIG. 1)

These three USP dissolution test methods were used to test isotretinoin containing drug product sold in the USA:

Absorica® (see composition in Table XII) product with no food effect as described in the product monograph, and Claravis® and/or Amnesteem®, which are both products with food effect.

Firstly, the dissolution method USP #1 uses the disintegration equipment. This is a 2 tier method which comprises a 30 minute capsule soaking in a simulated gastric fluid with pepsin followed by a 60 minute disintegration period in a medium brought to pH 10 with the addition of NaOH 0.13N. The isotretinoin concentration as a function of time is measured by spectroscopy UV at 343 nm. The specification is NLT 80% (Q) at 90 minutes.

This media while able to totally dissolve the Absorica® capsules in 60 minutes lacks discrimination power as it does not distinguish between isotretinoin capsules with food effect (Claravis®/Amensteem®) and without food effect (Absorica®).

Secondly, the dissolution method USP #2 is carried out at pH 7.8 buffer containing 0.5% w/v of surfactant N,N-Dimethyldodecylamine N-oxide using USP apparatus #1 (basket) at a speed of 100 rpm and a temperature of 37° C. The duration of the test is 90 minutes and the specification is NLT 80% (Q) at 90 minutes. Samples are analyzed by HPLC. Upon completion of the test after 90 minutes the following observations were made:

1. Only about 50% for the 10 mg capsules and about 40% for the 40 mg capsules of the without-food-effect isotretinoin capsules Absorica® are dissolved.
2. The variability of the results is extremely high: from 4% to 83% for 10 mg Absorica® capsules and from 11% to 60% for the 40 mg Absorica® capsules.

For these reasons it was decided that this method is insufficient for the testing of the without-food-effect isotretinoin capsules (Absorica®), namely, the capsule did not dissolve during the specified period of time and the extremely large variability.

Lastly, the dissolution method USP #3 uses borate buffer at pH 8.0, cetrimide and pancreatin. The test is performed using USP apparatus #2 (paddles) at 75 rpm. The isotretinoin is determined by HPLC and the test is successful if after 90 min 70% (Q) is released.

This method is able to dissolve the isotretinoin of the Absorica® capsules within the specified time but is not able to distinguish between isotretinoin containing capsules with food effect (Claravis®) and without food effect (Absorica®).

TABLE XVII

ISOTRETINOIN-CONTAINING CAPSULES USP DISSOLUTION TEST
Summary of CIP Dissolution using Different Dissolution Methods

| Food Effect | Method | USP 1 | USP 2 | USP 3 |
|---|---|---|---|---|
| | Media | SGF/NaOH 0.13N | Buffer | Buffer (borate) |
| | pH | 10.0 | 7.8 | 8.0 |
| | Surfactant | — | N,N-Dimethyl-dodecylamine N-oxide | Cetrimide |
| | Enzymes | Pepsin for 30 min | — | Pancreatin |
| | Equipment | Disintegration | Paddle | Paddle |
| | Speed | | 100 rpm | 75 rpm |
| | Duration | 30 + 60 min | 90 min | 90 min |
| | Analysis | UV-> + 343 min | HPLC | HPLC |
| | Specification | Q80% @ 90 min | Q80% @ 90 min | Q70% @ 90 min |
| NO | Absorica ® 10 mg | — | >53 | 99 |
| | Absorica ® 40 mg | 103 | >38 | 87 |
| YES | Amnesteem 10 mg | — | — | 25 |
| | Amnesteem 20 mg | 91 | — | — |
| | Claravis 10 mg | — | 103 | 75 |
| | Claravis 20 mg | — | — | — |
| | Claravis 40 mg | 95 | 93 | |
| | Conclusions: Able to distinguish between: | | | |
| • | Food/Non Food | No | No | No |

From those results it is concluded that none of the dissolution tests for isotretinoin capsules described in the USP are able to differentiate between the capsules with and without food effect.

Another dissolution test was performed using a dissolution media claimed by some to be designed to detect formulations with food effect.

Dissolution tests were performed on Absorica® capsules (on isotretinoin-containing capsules without food effect) using dissolution media simulating gastro intestinal fasted and fed states. This study used the dissolution media as indicated in Margareth Marque's article: "Dissolution Media Simulating Fasted and Fed States" as appears in Dissolution Technologies May 2004 Volume 11 Issue 2. The contents of this article are incorporated herein in their entirety for its teaching of dissolution media and their preparation and use.

Preparation of fasted state simulating intestinal fluid (FaSSIF) and fed state simulating intestinal fluid (FeSSIF) media.

Fasted State Simulated Intestinal Fluid (FaSSIF)

This media has a pH of 6.50 and an osmolality of about 270 mOsmol/kg.

Preparation of Blank FaSSIF

Dissolve 1.74 g of NaOH (pellets), 1.977 g of $NaH_2PO_4 \cdot H_2O$ or 17.19 g of anhydrous $NaH_2PO_4$, and 30.93 g of NaCl in 5 L of purified water. Adjust the pH to exactly 6.5 using 1 N NaOH or 1 N HCl.

Preparation of FaSSIF

Dissolve 3.3 g of sodium taurocholate in 500 mL blank FaSSIF. Add 11.8 mL of a solution containing 100 mg/mL lecithin in methylene chloride, forming an emulsion. The methylene chloride is eliminated under vacuum at about 40° C. Draw a vacuum for fifteen minutes at 250 mbar, followed by 15 minutes at 100 mbar. This results in a clear micellar solution, having no perceptible odor of methylene chloride. After cooling to room temperature, adjust the volume to 2 L with blank FaSSIF.

Fed State Stimulated Intestinal Fluid (FeSSIF)

This media has a pH of 5.00 and an osmolality of about 670 mOsmol/kg.

Preparation of Blank FeSSIF

Dissolve 20.2 g of NaOH (pellets), 43.25 g of glacial acetic acid, and 59.37 g of NaCl in 5 L of purified water. Adjust the pH to exactly 5.0 using 1 N NaOH or 1 N HCl.

Preparation of FeSSIF

Dissolve 16.5 g of sodium taurocholate in 500 mL of blank FeSSIF. Add 59.08 mL of a solution containing 100 mg/mL lecithin in methylene chloride, forming an emulsion. The methylene chloride is eliminated under vacuum at about 40° C. Draw vacuum for fifteen minutes at 250 mbar, followed by 15 minutes at 100 mbar. This results in a clear to slightly hazy, micellar solution having no perceptible odor of methylene chloride. After cooling to room temperature, adjust the volume to 2 L with blank FeSSIF.

The dissolution of Isotretinoin 40 mg Absorica® capsules was carried out in 500 mL of FaSSIF media and in 1000 mL of FeSSIF media using the USP Apparatus #2 (Paddles), at 100 rpm and 37° C. Dissolution samples were taken after 1 and 2 hours, and diluted to 50% with Acetonitrile. 90 μL were injected into an HPLC equipped with a UV detector at 353 nm, using a 5 μm 12.0 cm×4 mm C18 Column (like Lichrocart 100RP-18 endcapped or equivalent). The flow rate was 2.0 mL/min of mobile phase consisting of Acetonitrile:Water:Glacial Acetic Acid (85:15:0.5) at a temperature of 40° C. The samples were compared to an isotretinoin standard solution of known concentration.

TABLE XVIII

Results of Absorica ® Capsules in fasted simulating media

| Time (min) | Unit 1 | Unit 2 | Unit 3 | Mean | RSD |
|---|---|---|---|---|---|
| 60 | 13.8 | 11.4 | 9.4 | 12 | 19 |
| 120 | 15.7 | 16.4 | 13.2 | 15 | 11 |

The fasted simulating media (FaSSIF) only dissolves 15% of Absorica® 40 mg capsules after 2 hours.

TABLE XIX

Results of Absorica ® Capsules in fed simulating media

| Time (min) | Unit 1 | Unit 2 | Unit 3 | Mean | RSD |
|---|---|---|---|---|---|
| 60 | 12.1 | 12.4 | 12.6 | 12 | 2.1 |
| 120 | 17.1 | 16.9 | 20 | 18 | 9.8 |

The Fed simulating media (FeSSIF) only dissolve 18% of Absorica® 40 mg capsules after 2 hours.

From this experiment it is concluded that the simulated fasted and fed dissolution media are insufficiently capable of determining the food dependence of an isotretinoin-containing drug products without food effect, such as Absorica®, since media is unable to dissolve said Absorica® 40 mg capsules.

All these trials demonstrate that for isotretinoin drug products none of the dissolution test methods available to one skilled in the art are able to distinguish between formulation with and without food effect.

The use of the dissolution method of Example 3 is of great importance for the optimization of dosing conditions and product formulation since it can differentiate between isotretinoin formulations with or without significant food effect.

In addition, this biorelevant dissolution test could be used to assess bioequivalence of post-approval formulation changes in drug product form.

Modifications and changes may be made to the above-described embodiments without departing from the spirit and the scope of the present invention.

What is claimed is:

1. An oral pharmaceutical composition, comprising isotretinoin, and at least an oil and a glycerol macrogolglyceride of HLB of at least 10, wherein said oral pharmaceutical composition is substantially devoid of food effect when the amount of isotretinoin dissolved attains at least 70% of the oral pharmaceutical composition after about four hours of dissolution in a USP dissolution apparatus number 2 at a paddle speed of 100 rpm, and a dissolution media composed of 900 ml of pH 7.5 buffer containing 0.11% pancreatin, 4.7% cholic acid, 0.14% sodium dihydrogen phosphate and 0.5% sodium hydroxide at 37° C.

2. The oral pharmaceutical composition of claim 1, wherein the glycerol macrogolglyceride comprises from about 20% to about 80% by weight of the pharmaceutical composition.

3. The oral pharmaceutical composition of claim 1, wherein the oil comprises one or more of vegetable oils, medium chain triglycerides, fatty acid esters, amphiphilic oil, glycerol oleate compound, and/or mixtures thereof.

4. The oral pharmaceutical composition of claim 3, wherein the oil comprises from about 5% to about 70% by weight of the pharmaceutical composition.

5. The oral pharmaceutical composition of claim 1, wherein the glycerol macrogolglyceride has an HLB value of greater than 12.

6. The oral pharmaceutical composition of claim 1, which further comprises at least one surfactant.

7. The oral pharmaceutical composition of claim 1, which further comprises at least one disintegrant.

8. The oral pharmaceutical composition of claim 1, wherein 6 capsules containing said composition are 92% dissolved in view of the parameters set forth in Table XIII of the present specification.

9. The oral pharmaceutical composition of claim 1, which is in semi-solid form and is contained in a capsule.

10. The oral pharmaceutical composition of claim 9, wherein said capsule comprises a hard gelatin capsule, soft gelatin capsule, hypromellose capsule or starch capsule.

11. The oral pharmaceutical composition of claim 1, wherein the glycerol macrogolglyceride comprises lauroyl Macrogol-32 glycerides or stearoyl Macrogol-32 glycerides.

12. The oral pharmaceutical composition of claim 1, wherein the oily vehicle comprises soybean oil.

13. The oral pharmaceutical composition of claim 1, which comprises isotretinoin, stearyl Macrogol glycerides, soybean oil, sorbitan monooleate and propyl gallate.

14. The oral pharmaceutical composition of claim 1, wherein said substantially devoid of food effect is no significant food effect.

* * * * *